(12) United States Patent
Zeidner et al.

(10) Patent No.: US 9,468,208 B2
(45) Date of Patent: *Oct. 18, 2016

(54) DISEASE CONTROL WITH TICK PHOSPHOLIPASE A2

(71) Applicant: The United States of America, as represented by the Secretary, Department of Health and Human Services, Washington, DC (US)

(72) Inventors: Nordin Zeidner, Fort Collins, CO (US); Marc Dolan, Fort Collins, CO (US); Donald Champagne, Athens, GA (US)

(73) Assignees: University of Georgia Research Foundation, Inc., Athens, GA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/249,503

(22) Filed: Apr. 10, 2014

(65) Prior Publication Data

US 2014/0219985 A1  Aug. 7, 2014

Related U.S. Application Data

(62) Division of application No. 13/143,555, filed as application No. PCT/US2010/020513 on Jan. 8, 2010, now Pat. No. 8,735,126.

(60) Provisional application No. 61/143,304, filed on Jan. 8, 2009.

(51) Int. Cl.
*A61K 38/46* (2006.01)
*C12N 9/20* (2006.01)
*A01N 37/46* (2006.01)
*A61K 38/00* (2006.01)

(52) U.S. Cl.
CPC ............. *A01N 37/46* (2013.01); *A61K 38/465* (2013.01); *C12N 9/20* (2013.01); *C12Y 301/01004* (2013.01); *A61K 38/00* (2013.01)

(58) Field of Classification Search
CPC ................................ A61K 38/465; C12N 9/20
See application file for complete search history.

(56) References Cited

U.S. PATENT DOCUMENTS

| | | | |
|---|---|---|---|
| 5,470,712 A | 11/1995 | Simpson et al. | |
| 5,874,079 A * | 2/1999 | Weinrauch | C07G 17/00 424/94.1 |
| 6,528,051 B2 | 3/2003 | Tamarkin et al. | |
| 6,703,025 B1 * | 3/2004 | Patti | A61K 39/085 424/184.1 |
| 8,735,126 B2 * | 5/2014 | Zeidner | C12N 9/20 435/198 |
| 2003/0170257 A1 | 9/2003 | Trimnell et al. | |

OTHER PUBLICATIONS

Steen, N.A. et al.; Proteins in the Saliva of the Ixodida (ticks): Pharmacological Features and Biological Significance; Toxicon, Jan. 2006, vol. 47, Issue 1; pp. 1-20.

Zeidner, N. et al.; A Borreliacidal Factor in Amblyoma Americanum Saliva is Associated with Phospholiphase A2 Activity, Exp. Parasitol., Apr. 2009; vol. 121, No. 4; pp. 370-375.

Ledin et al., Medical and Veterinary Entomology, "Borreliacidal acivity of saliva of the tick Amblyomma americanum", (2005) 19, 90-95.

Bowman et al., Experimental Parasitology, "A novel phospholipase A2 activity in saliva of the lone star tick, *Amblyomma americanum* (L.)", (1997) 87, 121-132.

* cited by examiner

*Primary Examiner* — Ruth Davis
(74) *Attorney, Agent, or Firm* — Dinsmore & Shohl LLP; Weston R. Gould

(57) ABSTRACT

The present invention relates to reagents and methods for the modulation of viability of bacteria. A process is provided wherein a protein sequence from *A. americanum* saliva effective in reducing the viability of gram positive, gram negative, or acid-fast bacteria and spirochetes including *B. burgdorferi* is administered. The inventive protein from *A. americanum* saliva has utility as a therapeutic for the treatment of an organism infected with bacteria, particularly the spirochete *B. burgdorferi*.

10 Claims, 7 Drawing Sheets

A

B

DISEASE CONTROL WITH TICK PHOSPHOLIPASE A2

CROSS REFERENCE TO RELATED APPLICATIONS

This application is a divisional of U.S. patent application Ser. No. 13/143,555, filed Jul. 7, 2011, which claims priority from U.S. Provisional Application No. 61/143,304 filed Jan. 8, 2009, the entire contents of each of which are incorporated herein by reference.

FIELD OF THE INVENTION

The present invention relates generally to the field of pharmaceutical and diagnostic compositions useful in the diagnosis, treatment and prophylaxis of Lyme borreliosis. More specifically the present invention relates to methods of preparation of, sequence relating to, and use of phospholipase $A_2$ or phospholipase $A_2$-like protein derived from the tick *Amblyomma americanum*.

BACKGROUND OF THE INVENTION

*Borrelia burgdorferi* (sensu lato) encompasses several *Borrelia* species believed to be the causative agent of Lyme borreliosis (Lyme disease) including: *B. burgdorferi sensu strict; B. garinii*; and *B. afzelii*. Lyme disease is transmitted by the bite of various species of *Ixodes* ticks carrying the spirochete. The main reservoir of the infection in the United States is the white footed mouse, *Peromyscus leucopus*, and the infection can be transmitted to many mammalian species including dogs, cats, and man. (J. G. Donahue, et al, Am. J. Trop. Med. Hyg., 36:92-96 (1987); R. T. Green, et al, J. Clin. Micro., 26:648-653 (1988)).

*Amblyomma americanum* (Linnaeus), the lone star tick, is the primary vector of *Ehrlichia chaffeensis*, the bacterial agent of human monocytic ehrlichiosis (Anderson et al., 1993). In addition to *Ehrlichia chaffeensis* this aggressive human-biting tick species is also thought to vector other potential pathogens including *Ehrlichia ewingii, Rickettsia rickettsii, R. amblyominii, Borrelia lonestari, Francisella tularensis* and *Coxiella burnetii* (Calhoun, 1954; Burgdorfer, 1975; Barbour et al., 1996; Murphy et al., 1998; Burkot et al., 2001; Childs & Paddock, 2003). While *Amblyomma americanum* is found throughout geographical regions with a high occurrence of Lyme disease (Bishopp & Trembley, 1945; Anderson & Magnarelli, 1980; Hair & Bowman, 1986; Ginsberg et al., 1991; Luckhart et al., 1991; Keirans & Lacombe, 1998), there is no evidence that *A. americanum* transmits *B. burgdorferi* (Piesman & Happ, 1997). Reasons explaining why *A. americanum* fails to act as a suitable vector for *B. burgdorferi* have remained elusive.

Generally, arthropod vector refractoriness to a pathogen can be classified into three categories: (1) a lack of acquisition; (2) an inability to maintain growth of the pathogen; or (3) an inability to transmit the pathogen. In controlled experimental studies, as many as 25% of *A. americanum* larvae acquired spirochetes during infectious feedings. However, nearly all of these larvae were spirochete-negative before moulting to the nymphal stage (Piesman & Sinsky, 1988; Mather & Mather, 1990; Ryder et al., 1992; Piesman & Happ, 1997). Indeed, the refractory nature of *A. americanum* to maintaining and transmitting spirochetes has been previously recognized. Only one report of trans-stadial maintenance of infection in *A. americanum* nymphs has been published (Ryder et al., 1992), and one report of spirochete isolates from three pools of *A. americanum* adults (Teltow et al., 1991). However, these studies predate the discovery of the spirochete *B. lonestari*, or used methods that would not be able to discriminate between the two spirochete species, *B. burgdorferi* and *B. lonestari* (Barbour et al., 1996). Importantly, there has been no successful reported transmission of *B. burgdorferi* between infected and naïve hosts by *A. americanum* (Mukolwe et al., 1992; Ryder et al., 1992; Oliver et al., 1993; Sanders & Oliver, 1995; Piesman & Happ, 1997).

During *A. americanum, I. scapularis* and other Ixodid tick feeding, saliva is continuously secreted into the host (McMullen & Sauer, 1978; Coons et al., 1986; Sonenshine, 1991). A possible mechanism regulating transfer of *B. burgdorferi* has been previously identified as a factor in the saliva of *A. americanum*. (Ledin, K. E., et al., Med. Vet. Entomol., 2005; 19(1):90-95. However, specific molecules responsible for preventing transmission of *B. burgdorferi* during tick feeding are unknown making design and implementation of therapeutic methods and reagents difficult. Thus, there exists a need for identification of agents capable of controlling infection, growth, and viability of *B. burgdorferi.*

SUMMARY OF THE INVENTION

The present invention provides process for modulating a bacterium by administering a salivary protein of the tick *A. americanum* with phospholipase $A_2$-like activity. The protein preferably has a migratory molecular weight between 53 and 69 kDa. Several bacterial organisms are modulated by the invention. Preferably the bacterial organism is a member of the Spriochaetaceae family or the Treponemataceae family. More preferably, the bacterial organism is *Borrelia burgdorferi, Borrelia crocidurae, Borrelia lusitaniae, Borrelia recurrentis, Borrelia hermsii, Borrelia parkeri, Borrelia lonestari, Borrelia afzelii, Borrelia garinii, Borrelia recurrentis, Borrelia buccalis, Borrelia refringens, S. aureus, E. coli, L. monocytogenes, S. choleraesuis, S. typhi, S. enteritidis, S. pullorum, Bacillus anthracis*, or *M. tuberculosis*.

A therapeutic is provided that includes a suitable pharmaceutical carrier and a phospholipase $A_2$-like protein derived from *A. americanum*. The therapeutic is operable for treating Lyme disease in a vertebrate host. As such an inventive process of treating Lyme disease in a vertebrate host or modulating a *Borrelia burgdorferi* infection is provided including administering the therapeutic including the phospholipase $A_2$-like protein derived from *A. americanum*. The inventive therapeutic is administered at concentrations from about 0.05 to about 10,000 micrograms/milliliter. These concentrations are optionally maximal plasma concentrations. The inventive process optionally includes administering the therapeutic between one and three times per day.

BRIEF DESCRIPTION OF THE DRAWINGS

FIG. 1 represents fluorescent microscopy indicating live (SYTO9, white) and dead (propidium iodide, gray) staining as a measure of *B. burgdorferi* survival 48 h after exposure to specific in vitro treatments (100× magnification). (A) PBS, (B) *I. scapularis* saliva, (C) Pilocarpine, (D) Phospholipase $A_2$ derived from *A. americanum* saliva;

FIG. 2 represents (A) Mean live *B. burgdorferi* counts per 10 high powered (100×) fields and estimated 95% confidence intervals after exposure to phospholipase $A_2$ derived from *A. americanum* saliva, pilocarpine, *I. scapularis* saliva, or PBS at 24 and 48 h post-exposure;

DETAILED DESCRIPTION OF THE PREFERRED EMBODIMENTS

Figure 1:
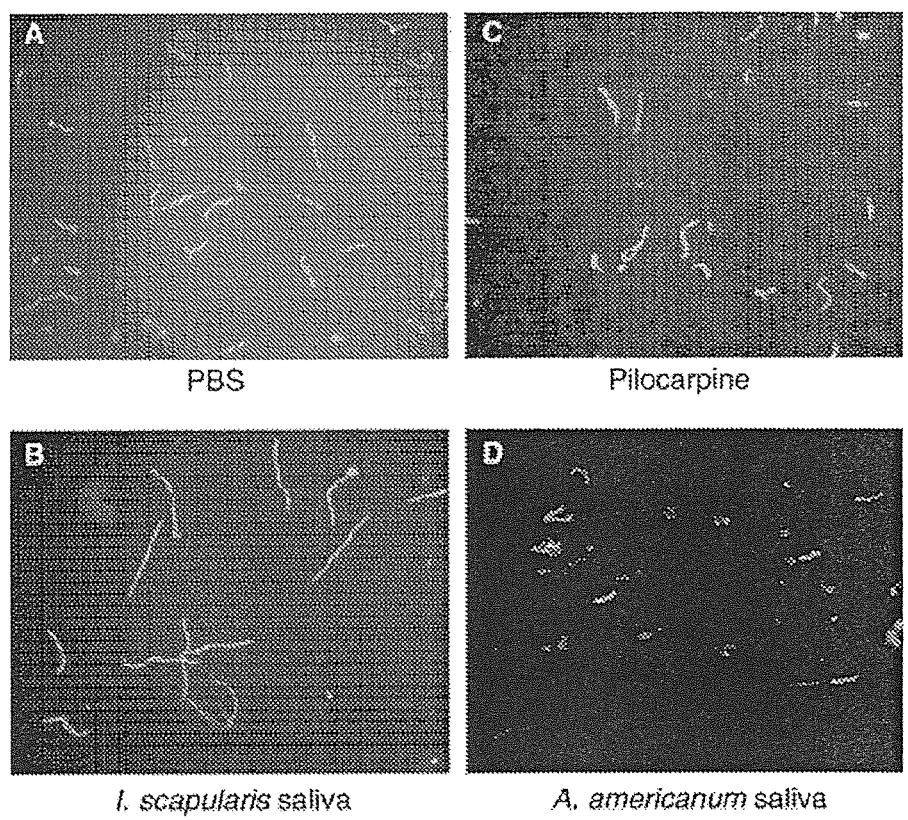
Figure 2:
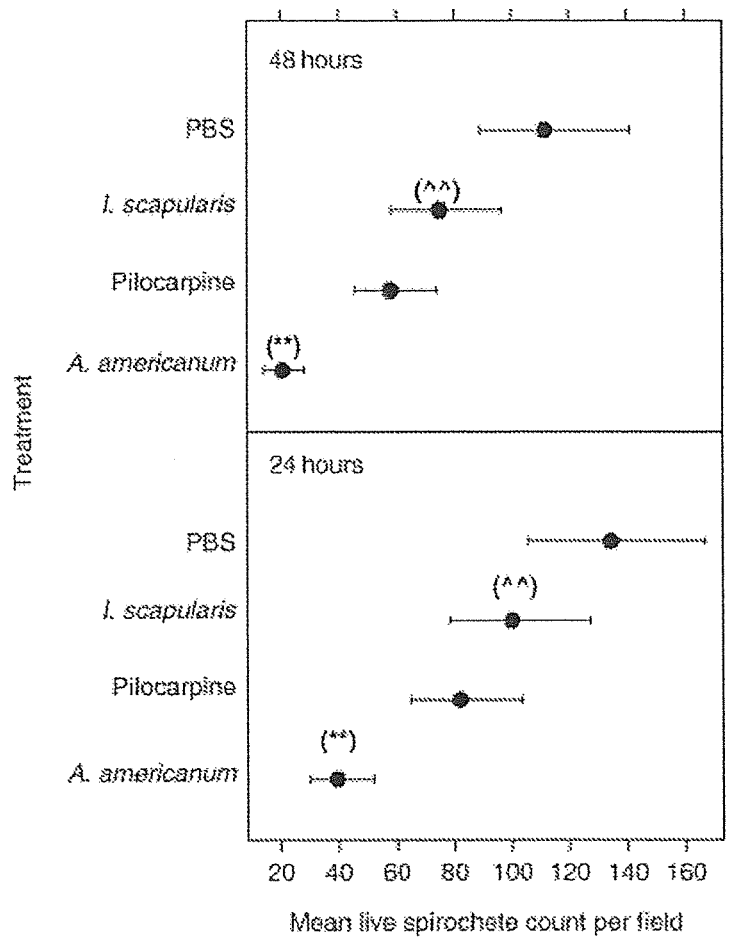
Figure 3:
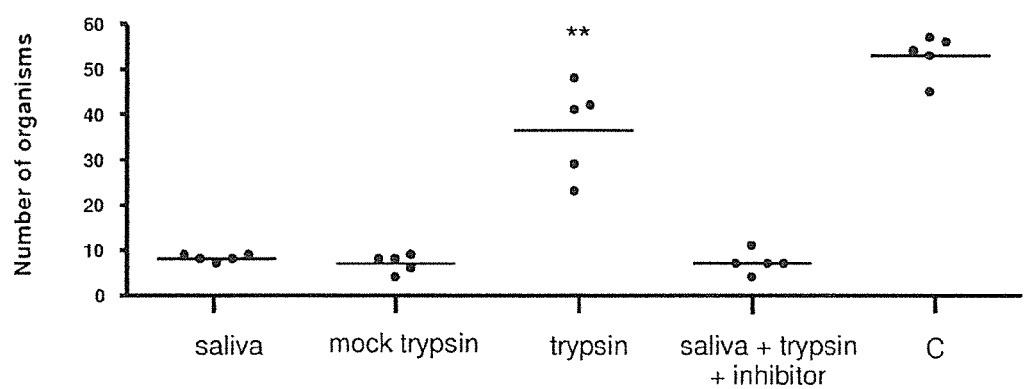
FIG. 3 represents elimination of borreliacidal activity in *A. americanum* saliva after incubation with trypsin.
Figure 4:
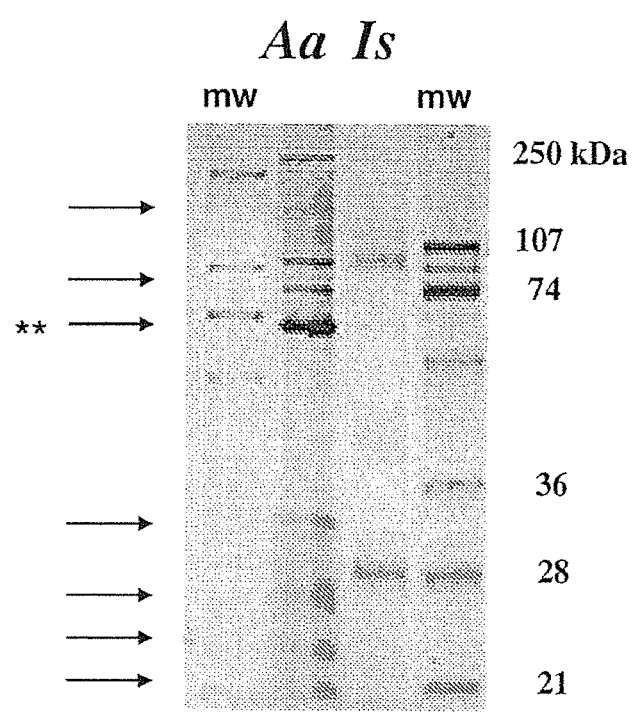
FIG. 4 represents comparative protein profiles of *A. americanum* and *I. scapularis* saliva as demonstrated by PAGE.
Figure 5:
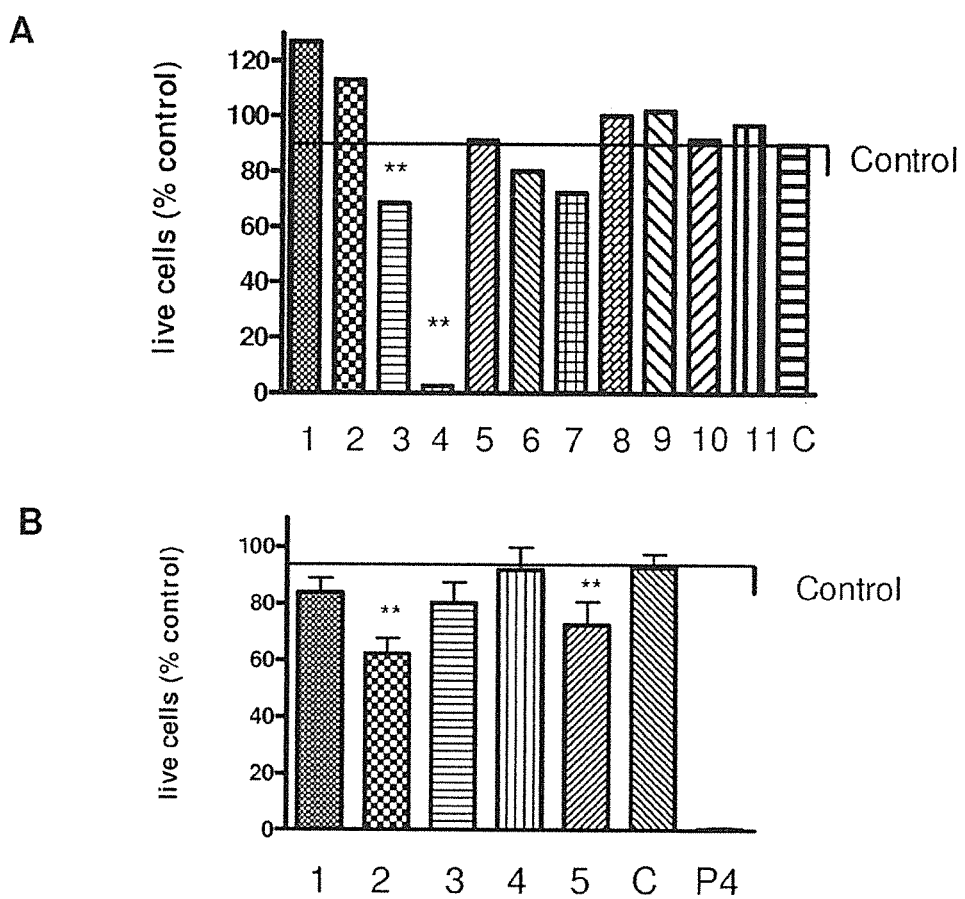
FIG. 5 represents (A) Borreliacidal activity of pools (1-11) of *A. americanum* saliva after fractionation by gel filtration HPLC and (B) Borreliacidal activity of *A. americanum* saliva fractions.

The present invention describes a novel nucleotide encoding a protein that resembles phospholipase $A_2$ from the tick *A. americanum*, and the protein derived therefrom, that has effectiveness in modulating an activity of a bacterial organism, illustratively, altering the viability of spirochetes and other bacterial organisms. Illustratively, the invention regulates viability of the Lyme disease spirochete *B. burgdorferi* or bacteria illustratively including *S. aureus*, *E. coli*, and *L. monocytogenes*. Thus, the invention has utility in regulating viability of spirochetes and bacteria.

The following description of the preferred embodiment(s) is merely exemplary in nature and is in no way intended to limit the scope of the invention, its application, or uses. The invention is described with relation to the non-limiting definitions included herein. These definitions are not designed to function as a limitation on the scope or practice of the invention but are presented for illustrative and descriptive purposes only.

The effectiveness of a phospholipase $A_2$-like protein (PLA2) in modulating *B. burgdorferi* viability was unexpected given that PLA2 preferably has a migratory molecular weight between 53 and 69 kDa. More preferably PLA2 has a migratory molecular weight between 58 and 62 kDa. It is appreciated that an inventive PLA2 protein is optionally monomeric or polymeric. Optionally the PLA2 protein is monomeric, dimeric, trimeric, pentameric, or hexameric. Previously described prior art phospholipase $A_2$ molecules have much lower molecular weights commonly between 14-15 kDa. While the mechanism may not be entirely tied to the protein length or molecular weight and lower molecular weight fragments of PLA2 are similarly operable, the mechanism of action of the *A. americanum* PLA2 of the present invention has unique functional properties that distinguish it from its mammalian counterparts allowing for low toxicity and cross reactivity when administered to a subject such as to treat a disease or infection.

The present invention provides methods and compositions for treating conditions or disorders having a relationship to infection of an organism by a spirochete or other bacteria. Illustrative examples of infectious agents addressed by administration or exposure to an inventive compound or material include those of the Spirochaetaceae family including the *Borrellia* genus and the *Treponema* genus. Illustratively organisms that may be targeted by the inventive compound or method include *B. burgdorferi*, *Borrelia crocidurae*, *Borrelia lusitaniae*, *Borrelia recurrentis*, *Borrelia hernisii*, *Borrelia parkeri*, *Borrelia lonestari*, *Borrelia afzelii*, *Borrelia garinii*, *Borrelia recurrentis*, *Borrelia buccalis*, and *Borrelia refringens*. *B. burdorferi* is most preferred.

Members of the genus *Leptospira* are similarly amenable to modulation by the inventive compound. Illustratively, serovars Icterohaemorrhagiae, Canicola, Pomona, Grippotyphosa, and Bratislava are amenable to modulation.

It is recognized that many other members of the Sprirochaetaceae family, the Treponemataceae family, and other bacterial organisms are known and are recognized as similarly targetable by the present invention. Members of human pathogen groups *Leptospira* (non-limiting ex. *L. interrogans*, *L. canicol*, *L. biflexia*), *Borrelia*, and *Treponema* are particularly preferred.

Non spirochete organisms are similarly targetable by the present invention. Organisms illustratively include *S. aureus*, *E. coli*, *L. monocytogenes*, *S. choleraesuis*, *S. typhi*, *S. enteritidis*, *S. pullorum*, *Bacillus anthracis*, *M. tuberculosis*, and other gram positive bacteria.

Diseases caused by agents that may be illustratively modulated by the present invention include but are not limited to Lyme disease, relapsing fever, leptospirosis, rat bite fever, Vincent's angina, syphilis, yaws, pinta, periodontal disease, oral soft tissue infections, fusospirochetal disease, conjunctivitis, septicemia, granulomatosis infantisepticum, listeriosis, tuberculosis, and anthrax.

As used herein, the terms "subject" or "organism" are treated synonymously and are defined as any organism capable of hosting infection of a spirochete or bacteria. A subject illustratively includes a mammal, humans, non-human primates, horses, goats, cows, sheep, pigs, dogs, cats, rodents, arthropods, ticks, and cells.

A therapeutically effective amount is defined as an amount of an inventive compound that when administered to a subject, ameliorates a condition or symptom of infection.

The terms "biologically active peptide" and "peptide therapeutic agent," "peptide," and "protein" are synonymous as used herein and are intended to mean a natural or synthetic compound containing two or more amino acids, particularly protein that participates in modulating an aspect of a target organism, illustratively, a bacterial organism. It is appreciated that a protein optionally has fewer or more amino acids than the wild-type sequence. Amino acids present in a protein illustratively include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the term "biologically active peptide" as used herein includes peptides having between 2 and about 1000 amino acids or having a molecular weight in the range of about 150-100,000 Daltons.

A biologically active peptide is obtained by any of various methods known in the art illustratively including isolation from a cell or organism, chemical synthesis, expression of a nucleic acid and partial hydrolysis of proteins. Chemical methods of peptide synthesis are known in the art and include solid phase peptide synthesis and solution phase peptide synthesis for instance. A biologically active peptide included in an inventive composition may be a naturally occurring or non-naturally occurring peptide. The term "naturally occurring" refers to a peptide endogenous to a cell, tissue or organism and includes allelic variations. A non-naturally occurring peptide is synthetic or produced apart from its naturally associated organism or modified and is not found in an unmodified cell, tissue or organism.

The term "biological activity" as used herein is intended to mean an activity usually associated with a peptide or nucleic acid. Biological activity includes activity described at a molecular level such as receptor binding/blocking, receptor activation/inhibition, ion channel modulation, second messenger modulation, and membrane disruption. Biological activity further includes activity described at a cellular or subcellular level such as stimulation/inhibition of synaptic release. In addition, biological activity further includes activity described at an organismal level such as behavioral changes, changes in perception of pain, and decreased nausea and/or vomiting. Biological activity of a peptide is measurable and may be assessed by techniques known in the art.

As used herein, the term "sample" is defined as material obtained from a biological organism, tissue, cell, cell culture medium, or any medium suitable for mimicking biological conditions, or from the environment. Non-limiting examples include, saliva, gingival secretions, cerebrospinal fluid, gastrointestinal fluid, mucous, urogenital secretions, synovial fluid, cerebrospinal fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, water, air, gas, powder, soil, biological waste, feces, cell culture media, cytoplasm, cell releasate, cell lysate, buffers, or any other fluid or solid media.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably in this application.

An inventive nucleic acid sequence is provided. The nucleic acid sequence relates to the gene encoding PLA2 derived from the tick A. americanum. The nucleic acid sequence preferably encodes salivary PLA2 derived from the tick *A. americanum*. The inventive nucleic acid sequence is preferably isolated from the cellular materials with which it is naturally associated. It is appreciated that a nucleic acid sequence that hybridizes with a nucleic acid sequence encoding PLA2 protein is within the scope of the invention. A hybridizing nucleic acid sequence optionally has a sequence 100 percent complementary to a nucleic acid sequence encoding PLA2 or a portion thereof. Optionally, a hybridizing nucleic acid sequence has 50, 60, 70, 80, 90, 95, 99, or greater complementarity to a nucleic acid sequence encoding PLA2 or a fragment thereof.

As used herein, the term "hybridizes" preferably describes hybridization under stringent conditions for hybridization and washing under which nucleotide sequences having at least 30%, 35%, 40%, 45%, 50%, 55%, 60%, 65%, 70%, 75%, 80%, 85%, 90%, 95%, 99% or greater complementarity to each other typically remain hybridized to each other. Such hybridization conditions are described in, for example but not limited to, Current Protocols in Molecular Biology, John Wiley & Sons, N.Y. (1989), 6.3.1 6.3.6; Basic Methods in Molecular Biology, Elsevier Science Publishing Co., Inc., N.Y. (1986), pp. 75 78, and 84 87; and Molecular Cloning, Cold Spring Harbor Laboratory, N.Y. (1982), pp. 387 389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at 50 to 65° C.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cell systems known in the art as amenable to transfection and nucleic acid and/or protein expression. Methods of nucleic acid isolation are similarly recognized in the art. Illustratively, plasmid DNA amplified in *E. coli* is cleaved by suitable restriction enzymes such as NdeI and XhoI to linearize PLA2 DNA. The PLA2 DNA is subsequently isolated following gel electrophoresis using a S.N.A.P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The present invention includes variants of PLA2 such as allelic variants, mutational variants, insertional variants, deletion variants, or nucleotide variants illustratively including derivative nucleotides and amino acid variants. As used herein, the term "variant" defines either a naturally occurring genetic mutant of PLA2, or a recombinantly prepared variation of PLA2, each of which contain one or more mutations in its genome compared to the wild type PLA2. A variant optionally includes a derivative.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative also defined as a degenerate base mimicking a C/T mix such as that from Glen Research Corporation, Sterling, Va., illustratively LNA-dA or LNA-dT, or other nucleotide modification known in the art or otherwise. A nucleotide is optionally locked.

A nucleotide sequence variant is preferably greater than 50 percent identical to a nucleic acid sequence encoding PLA2 or a fragment thereof. More preferably, a nucleotide sequence variant is greater than 75 percent identical to a nucleic acid sequence encoding PLA2 or a fragment thereof. A nucleotide sequence variant is preferably 80, 85, 90, 95, 99 percent identical or greater to a nucleic acid sequence encoding PLA2 or a fragment thereof.

Similarly, an amino acid sequence variant is preferably greater than 50 percent identical to an amino acid sequence of PLA2 or a fragment thereof. More preferably, an amino acid sequence variant is greater than 75 percent identical to an amino acid sequence of PLA2 or a fragment thereof. An amino acid variant is preferably 80, 85, 90, 95, 99 percent identical or greater to an amino acid sequence of PLA2 or a fragment thereof.

It is recognized that several forms of phospholipase $A_2$ from numerous organisms exist as allelic variants. Illustratively, human lipoprotein associated phospholipase $A_2$ is found with known variants of −1357G>A, −403T>C, and variants producing amino acid substitutions Arg92His, Ile198Thr, Ala379Val. (Hoffmann, M M, et al., *J Thromb Haemost.*, 2009; 7(1):41-8) Similarly, allelic variants of PLA2 are recognized and within the scope of the present invention.

The nucleotide sequences of the invention are optionally isolated by conventional uses of polymerase chain reaction or cloning techniques such as those described in conventional texts. For example, the nucleic acid sequences of this invention are optionally prepared or isolated from DNA using DNA primers and probes and PCR techniques. Alternatively, the inventive PLA2 nucleic acid sequence is obtained from gene banks derived from *A. americanum* whole genomic DNA. These sequences, fragments thereof, modifications thereto and the full-length sequences are optionally constructed recombinantly using conventional genetic engineering or chemical synthesis techniques or PCR, and the like.

Modulation of bacterial target activity is illustratively accomplished with a fragment of PLA2. As the molecular weight of the protein encoded by a preferred embodiment of isolated PLA2 nucleotide sequence is 58-62 kDa and other forms of phospholipase A2 commonly range from 14-15 kDa, functional fragments of PLA2 are recognized as having activity toward modulating an aspect of a target organism such as viability.

As used herein the term "modulating" refers to altering a function, cycle, characteristic, or target of an infectious agent. Preferably, modulating is altering the viability of an organism. Modulating is optionally alteration of transcription, translation, molecular localization, modification, or activity.

The present invention also encompasses an isolated phospholipase $A_2$ protein derived from *A. americanum*. In a preferred embodiment an inventive PLA2 protein has the sequence represented by an amino acid sequence of PLA2 or a fragment thereof. PLA2 protein is preferably recombinant. However, it is also envisioned that naturally occurring PLA2 protein is optionally isolated from at least a portion of the cellular and other sample material for which the wild type sequence is normally found. Methods for purification of protein from organism derived samples are known and are within the level of skill in the art.

Modifications and changes can be made in the structure of the phospholipase $A_2$ protein derived from *A. americanum* that is the subject of the application to create a variant thereof and still obtain a molecule having similar characteristics as the phospholipase (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within +0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

An inventive PLA2 protein is illustratively recombinant. An inventive protein is optionally coexpressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to PLA2 or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished from transcription of PLA2 nucleic acid sequence, translation of RNA transcribed from PLA2 nucleic acid sequence, modifications thereof, or fragments thereof. Protein expression is preferably performed in a cell based system such as in *E. coli*, Hela cells, insect cells, or Chinese hamster ovary cells. Eukaryotic, are preferred. Insect cells are particularly preferred. It is appreciated that cell-free expression systems are similarly operable.

It is recognized that numerous variants, analogues, or homologues are within the scope of the present invention including amino acid substitutions, alterations, modifications, deletions, insertions, or other amino acid changes that increase, decrease, or do not alter the function of the PLA2 protein sequence. Several post-translational modifications are similarly envisioned as within the scope of the present invention illustratively including incorporation of a non-naturally occurring amino acid, phosphorylation, glycosylation, addition of pendent groups such as biotin, fluorophores, lumiphores, radioactive groups, antigens, or other molecules.

The present invention also provides a vector with an inventive PLA2 sequence therein. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is preferably a plasmid. A suitable vector optionally possesses cell type specific expression or other regulatory sequences or sequences operable to stimulate or inhibit gene or protein expression. A vector illustratively contains a selection marker such as an antibiotic resistance gene.

Also provided is a host cell transformed with an appropriate vector or with the inventive PLA2 sequence. A preferred host cell includes *E. coli* or Sf9 cells. Optionally cell transfection is achieved by electroporation.

A method is also provided for recombinantly expressing a inventive PLA2 nucleic acid or protein sequence or fragments thereof wherein a cell is transformed with an inventive nucleic acid sequence and cultured under suitable conditions that permit expression of PLA2 nucleic acid sequence or protein either within the cell or secreted from the cell. Cell culture conditions are particular to cell type and expression vector. Culture conditions for particular vectors and cell types are within the level of skill in the art to design and implement without undue experimentation.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual $3^{rd}$ ed. (Cold Spring Harbor, N.Y. 2001).

Some embodiments of the present invention are compositions containing PLA2 nucleic acid that can be expressed as encoded polypeptides or proteins. The engineering of DNA segment(s) for expression in a prokaryotic or eukaryotic system may be performed by techniques generally known to those of skill in recombinant expression. It is believed that virtually any expression system is operable for the expression of the claimed nucleic and amino sequences.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells that do not contain a recombinantly introduced exogenous DNA segment or gene. A host cell is optionally a naturally occurring cell that is transformed with an exogenous DNA segment or gene or a cell that is not modified. A host cell preferably does not possess a naturally occurring gene encoding PLA2. Engineered cells are, thus, cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide in accordance with the present invention one illustratively prepares an expression vector that includes a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* .chi. 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage preferably also contain, or be modified to contain, promoters that can be used by the microbial organism for expression of its own proteins.

In addition, phage vectors containing replicon or control sequences that are compatible with the host microorganism can be used as transforming vectors in connection with these hosts. For example, the phage lambda is optionally utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is illustratively used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to microorganisms, cultures of cells derived from multicellular organisms are also optionally used as hosts. In principle, any such cell is operable, whether from vertebrate or invertebrate culture. In addition to mammalian cells, these include insect cell systems such as those infected with recombinant virus expression vectors (e.g., baculovirus); and plant cell systems such as those infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051 incorporated herein by reference).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell type is optionally chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems are preferably chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication is optionally provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters are optionally derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems are optionally utilized, for example, commonly used promoters are derived from polyoma, Adenovirus 2, Adenovirus 5, cytomegalovirus and Simian Virus 40 (SV40). The early and late promoters of SV40 virus are useful because both are obtained easily from the virus as a fragment which also contains the SV40 viral origin of replication. Smaller or larger SV40 fragments are also optionally used, preferably provided there is included the approximately 250 bp sequence extending from the HindIII site toward the BglI site located in the viral origin of replication.

In cases where an adenovirus is used as an expression vector, the coding sequences are optionally ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals are optionally provided for efficient translation of the claimed isolated nucleic acid coding sequences. These signals illustratively include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons are optionally of a variety of origins, both natural and synthetic. The efficiency of expression is optionally enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides downstream of the termination site of the protein at a position prior to transcription termination.

For long-term, high-yield production of recombinant proteins, stable expression is preferred. Illustratively, cell lines that stably express constructs encoding proteins are engineered. Rather than using expression vectors that contain viral origins of replication, host cells are optionally transformed with vectors controlled by appropriate expression control elements (e.g., promoter, enhancer, sequences, transcription terminators, polyadenylation sites, etc.), and a selectable marker. Following the introduction of foreign DNA, engineered cells are illustratively allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems are optionally used, including, but not limited, to the herpes simplex virus thymidine kinase, hypoxanthine-guanine phosphoribosyl-transferase and adenine phosphoribosyltransferase genes, in tk⁻, hgprt⁻ or aprt⁻ cells, respectively. Also, antimetabolite resistance is optionally used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated nucleic acids of the disclosure are optionally overexpressed; i.e. expressed in increased levels relative to its natural expression in cells of its indigenous organism, or even relative to the expression of other proteins in the recombinant host cell. Such overexpression is illustratively assessed by a variety of methods, including radio-labeling and/or protein purification. However, simple and direct methods are preferred, for example, those involving SDS/PAGE and protein staining or immunoblotting followed by quantitative analyses such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell.

Further aspects of the present disclosure concern the purification, and in particular embodiments, the substantial purification, of an encoded protein or peptide. The term "purified" or "isolated" protein or peptide as used herein, is intended to refer to a composition, isolatable from other components, wherein the protein or peptide is purified to any degree relative to its naturally-obtainable state, i.e., in this case, relative to its purity within a cell of a tick salivary gland. A purified protein or peptide, therefore, also refers to a protein or peptide free from the environment in which it may naturally occur.

Generally, "purified" or "isolated" will refer to a protein or peptide composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of the protein or peptide will be known to those of skill in the art particularly in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation followed by centrifugation, chromatography steps such as ion exchange and the like, gel filtration, reverse phase, hydroxylapatite and affinity chromatography isoelectric focusing gel electrophoresis and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification is illustratively accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product or in maintaining the activity of an expressed protein.

It is known that the migration of a polypeptide can vary, sometimes significantly, with different conditions of SDS/PAGE (Capaldi et al., *Biochem. Biophys. Res. Comm.*, 76:425, 1977). It will, therefore, be appreciated that under differing electrophoresis conditions the apparent molecular weights of purified or partially purified expression products may vary.

It is recognized in the art that several phospholipase $A_2$ proteins gain their full activity when bound to phospholipid micelles or membranes, an effect known as interfacial activation (Scott, D. L., and Sigler, P. B. (1994) *Adv. Protein Chem.* 45, 53-88; Arni, R. K., and Ward, R. J. (1996) *Toxicon*, 34, 827-841; Berg, O. G., et al. (2001) *Chem. Rev.*, 101, 2613-2654) the contents of each of which are incorporated herein by reference. The N-terminal portion of phospholipase $A_2$ is believed to be essential for mediating this interaction (Qin, S., Pande, et al., (2004) *J. Mol. Biol.*, 344, 71-89). Additionally, the catalytic histidine ($His^{48}$) and functionally important tyrosine ($Tyr^{69}$) on the human phospholipase $A_2$ are encompassed by structural regions that are important for enzymatic substrate binding and catalytic activity (human phospholipase $A_2$ numbering). As such, the invention envisions fragments of PLA2 that allow for individual or combined activities such as membrane binding or catalytic function that are individually isolated or combined free of non-essential regions of the inventive PLA2 protein or nucleic acid sequence. The invention also envisions isolation of fragments of PLA2 encompassing regions with activities unique to phospholipase $A_2$ from *A. ainericanum*.

An inventive process illustratively includes isolation of PLA2 protein or nucleic acid sequence from a host cell or host cell medium. Methods of protein isolation illustratively include column chromatography, affinity chromatography, gel electrophoresis, filtration, or other methods known in the art. In a preferred embodiment PLA2 protein is expressed with a tag operable for affinity purification. A preferred tag is a 6×His tag. A 6×His tagged inventive protein is illustratively purified by Ni-NTA column chromatography or using an anti-6×His tag antibody fused to a solid support. (Geneway Biogech, San Diego, Calif.) Other tags and purification systems are similarly operable.

It is appreciated that an inventive protein is optionally not tagged. In this embodiment and other embodiments purification is optionally achieved by methods known in the art illustratively including ion-exchange chromatography, affinity chromatography using anti-PLA2 antibodies, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

An inventive PLA2 protein or fragment thereof is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis. Illustrative methods of chemical protein synthesis are reviewed by Miranda, L P, *Peptide Science,* 2000, 55:217-26 and Kochendoerfer G G, *Curr Opin Drug Discov Devel.* 2001; 4(2):205-14, the contents of each of which are incorporated herein by reference.

PLA2 proteins of this invention are optionally characterized by immunological measurements including, without limitation, western blot, macromolecular mass determinations by biophysical determinations, SDS-PAGE/staining, HPLC and the like, antibody recognition assays, cell viability assays, apoptosis assays, and assays to infer immune protection or immune pathology by adoptive transfer of cells, proteins or antibodies.

An inventive PLA2 protein of the present invention is optionally modified to increase its immunogenicity. In a non-limiting example, the antigen is coupled to chemical compounds or immunogenic carriers, provided that the coupling does not interfere with the desired biological activity of either the antigen or the carrier. For a review of some general considerations in coupling strategies, see Antibodies, A Laboratory Manual, Cold Spring Harbor Laboratory, ed. E. Harlow and D. Lane (1988) the contents of which are incorporated herein by reference for this and other relevant teaching. Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The inventive PLA2 protein is optionally modified by other techniques, illustratively including denaturation with heat and/or SDS.

A PLA2 protein of the present invention is optionally used in the form of a pharmaceutically acceptable salt. Suitable acids and bases which are capable of forming salts with the polypeptides of the present invention are well known to those of skill in the art and include inorganic and organic acids and bases.

In another aspect, the invention provides a therapeutic composition and methods for treating humans and/or animals with Lyme disease or infection with a spirochete. The therapeutic composition contains an inventive PLA2 protein, nucleic acid sequence, or fragment thereof as described above and a suitable pharmaceutical carrier.

The proteins and nucleic acid sequences or anti-sense sequences of the invention, alone or in combination with other antigens, antibodies, nucleic acid sequences or anti-sense sequences are optionally used in therapeutic compositions and in methods for treating humans and/or animals with spirochete or other bacterial disease illustratively including Lyme Disease. For example, one such therapeutic composition is formulated to contain a carrier or diluent and one or more PLA2 proteins or protein fragments of the invention. Suitable pharmaceutically acceptable carriers facilitate administration of the proteins but are physiologically inert and/or nonharmful.

Carriers are optionally selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

Optionally, the inventive composition contains conventional pharmaceutical ingredients such as preservatives or chemical stabilizers. Suitable ingredients operable herein include, for example, casamino acids, sucrose, gelatin, phenol red, N—Z amine, monopotassium diphosphate, lactose, lactalbumin hydrolysate, and dried milk.

Alternatively, or in addition to the PLA2 proteins of the present invention, other agents useful in treating Lyme disease, e.g., antibiotics or immunostimulatory agents and cytokine regulation elements, are expected to be useful in reducing or eliminating disease symptoms. Agents operable herein to suppress or counteract the immune suppressants released by the tick vector or the spirochete preferably act to assist the natural immunity of the infected human or animal. Thus, such agents optionally operate in concert with the therapeutic compositions of this invention. The development of therapeutic compositions containing these agents is within the skill of one in the art in view of the teachings of this invention.

According to the invention, a human or an animal is optionally treated for Lyme Disease or other spirochete or bacterial infection by administering an effective amount of such a therapeutic composition. An "effective amount" is preferably between about 0.05 to about 1000 μg/mL of an PLA2 protein. A suitable dosage is preferably about 1.0 mL of such an effective amount. Such a composition is optionally administered 1-3 times per day over a 1 day to 12 week period. However, suitable dosage adjustments may be made by the attending physician or veterinarian depending upon the age, sex, weight, composition pharmacokinetics, composition pharmakodynamics, and general health of the subject. Preferably, such a composition is administered parenterally, preferably intramuscularly or subcutaneously. However, an inventive composition is optionally formulated to be administered by any other suitable route, including orally or topically.

It is appreciated that the efficacy of the present invention is readily determined with respect to altering bacterial organism function by growing the organisms in culture and placing a spatially controlled and known amount of the inventive PLA2 into contact with the organism culture and then measuring an inhibition zone around the phospholipase. With culture efficacy, non-human animals infected with the bacterial organism are then administered the inventive phospholipase by known methods such as intravenous or intramuscular injection. Bacterial organism titers relative to a control provide in vivo efficacy and dosing regimes extendible to humans.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. The contents of each of the herein included references are incorporated herein by reference in their entirety.

The invention is further described by reference to the following detailed examples, wherein the methodologies are as described below. These examples are not meant to limit the scope of the invention that has been set forth in the foregoing description. Variations within the concepts of the invention are apparent to those skilled in the art.

Example 1

The cDNA of full-length *A. americanum* PLA2 is cloned from an *A. americanum* cDNA library and subcloned into the pET-21a(+) vector (Novagen, Madison, Wis.). The cDNA library is created from genomic DNA from *A. americanum* using the CloneMiner™ cDNA Library Construction Kit available from Invitrogen (Carlsbad, Calif.). Amplification and cloning of plasmids containing the cDNA for PLA2 is performed essentially as described by Wijewickrama, G T, et al., *J. Biol. Chem.*, 2006; 281(43):32741, the contents of which are incorporated herein by reference. All constructs are transformed into DH5α, cells for plasmid isolation, and their DNA sequences are verified. *E. coli* strain BL21 (DE3) was used as a host for the protein expression.

Example 2

Isolation and purification of PLA2. PLA2 is purified from *E. coli* BL21 (DE3). The plasmid encoding PLA2 adds an amino-terminal His tag for subsequent purification. Optionally, the His tag is cleavable by incorporation of a cleavage sequence for enzymes such as trypsin, factor Xa, or thrombin. The bacteria are grown overnight at 37° C. in 2 liters of LB broth supplemented with 100 mg/liter of ampicillin; harvested by centrifugation; suspended in 30 ml of 10 mM Tris.HCl (THCl), pH 8.3; and sonicated for 15 min on ice. The cell debris is removed by centrifugation at 20,000×g for 15 min, and the supernatant is loaded onto a Ni-NTA agarose (Qiagen) column (1.5×3 cm). The column is washed with 50 ml of 1.0 M NaCl in THCl, and the protein eluted with a 40-ml linear gradient of 0-0.25 M imidazole in THCl. Recombinant protein is identified by SDS/PAGE, and peak fractions are pooled. The protein is dialyzed against 3 liters of THCl at 4° C. overnight and loaded on a DEAE Sepharose column (1.5×5 cm) equilibrated with THCl. Protein is eluted with a 60-ml linear gradient of 0-0.15 M NaCl. The purified protein is again dialyzed against 3.5 liters of THCl. Purified recombinant PLA2 is free of contaminating proteins as assessed by Coomassie blue-stained SDS/PAGE. All reagents and glassware used for toxin purification and biological assays are pyrogen-free.

Example 3

Figure 6:
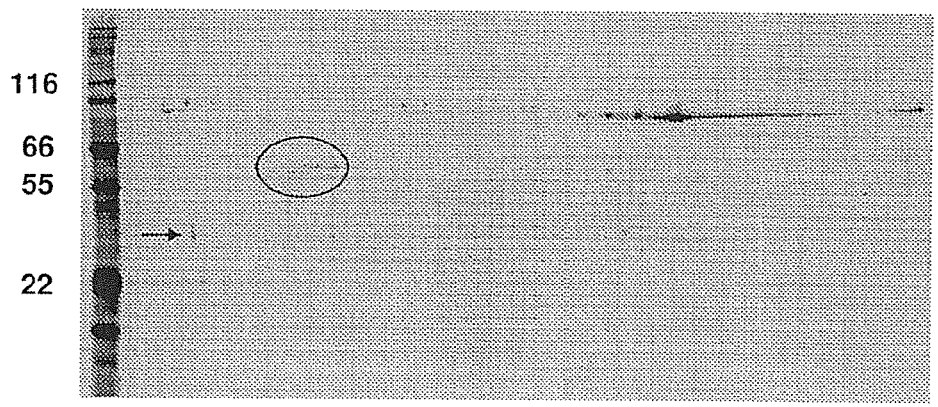
FIG. 6 represents (A) two dimensional gel electrophoresis of active borreliacidal fractions of *A. americanum* saliva and (B) two dimensional gel electrophoresis of inactive fractions of *A. americanum* saliva.
Figure 6:
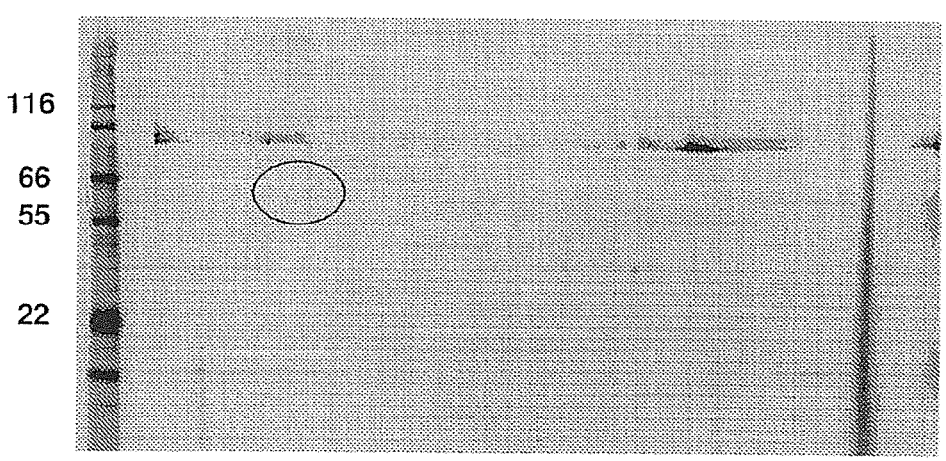

Evaluation of PLA2 protein regulation of *B. burgdorferi* viability. Analyses of PLA2 protein is performed essentially as described by Ledin, K. E., et al., Med. Vet. Entomol., 2005; 19(1):90-95, the contents of which are incorporated herein by reference. Frozen stocks of low-passage B31 *B. burgdorferi* isolates (Shelter Island, N.Y.) are reconstituted in BSK-H culture medium and maintained at 35° C. to log phase (Piesman, 1993). Spirochete cultures are diluted with BSK-H to a density of $4.7\times10^7$ viable spirochetes per mL as counted in a Petroff-Hauser chamber under dark-field microscopy, and distributed in 15 μL aliquots into 0.7 mL tubes for a total of $7.05\times10^5$ spirochetes per tube. A mean starting concentration of 155 live spirochetes per field is assessed prior to the addition of specific treatments. Each 15 μL aliquot of spirochetes in BSK-His treated with either 15 μL of sterile PBS, 15 μL of 1.33 mg/mL pilocarpine (based on the mid-range of pilocarpine found in previous analysis of tick saliva, (Ribeiro et al., 2004) in sterile PBS, or 15 μL of tick saliva, and incubated at 35° C. 10 μL samples taken from each of 10 prepared cultures and assessed for spirochete survival at 0, 24 and 48 h. Time points for spirochete survival assessment are chosen based on previous observations of post-feeding decreases in spirochete-positive ticks (Ryder et al., 1992).

Spirochete survival is evaluated by enumeration of spirochetes stained with the live/dead BacLight Viability Kit (Molecular Probes, Eugene, Oreg.). Briefly, fluorescence stains SYTO 9 (live stain) and propidium iodide (dead stain) are combined at a 1:100 dilution in sterile PBS (Invitrogen, Grand Island, N.Y.). A total of 0.5 μL of this solution is mixed with 10 μL from each spirochete culture. Stained cultures are suspended on a standard glass slide under a 22×22 mm cover slip and viewed at 100× magnification through FITC and rhodamine filters. Live and dead spirochetes are counted from 10 randomly chosen high-power fields per slide. Results are compared with the saliva of *I. scapularis* as a negative control. PLA2 protein in buffered saline is used as synthetic tick saliva.

Using this method live spirochetes stain green (FIGS. 1A and B) and can be readily visualized and distinguished from injured and dead spirochetes that stain red (FIGS. 1C and D). This analysis (FIG. 2) indicates that treatment with PLA2 protein significantly reduces the average number of live spirochetes at both 24 h (mean=39.6) and 48 h (mean=20.1) compared with both pilocarpine at 24 and 48 h (82.1/58.2) and PBS alone at 24 and 48 h (133/112) (all $P<0.001$). Furthermore, average counts for PLA2 are lower than average counts for *I. scapularis* treatment at 24 and 48 h (100.2/75.0, $P<0.001$ for both time points). In contrast, *I. scapularis* does not yield significantly different spirochete counts than pilocarpine at both time points, while demonstrating a significant killing effect compared to PBS at 24 and 48 h ($P<0.001$ for both).

Example 4

Incubation with trypsin eliminates *A. americanum* borreliacidal activity. Colony-produced, pathogen-free *A. americanum* adults are obtained from the Oklahoma State University Tick Rearing Facility (Stillwater, Okla.). Colony maintained, pathogen-free *I. scapularis* adults are obtained from the Tick Biology and Ecology Laboratory of the CDC (Fort Collins, Colo.). To collect saliva, adult New Zealand rabbits (Western Oregon Rabbit Company) are infested with 20-30 pairs of adult *A. americanum* or *I. scapularis* ticks, and saliva is collected beginning at the rapid engorgement phase for each tick species as previously described (Ledin et al., 2005). Saliva is then aliquoted and frozen at −80° C. until use.

Whole saliva is incubated with *B. burgdorferi* in the presence of 10 μg of bovine trypsin essentially as described in Zeidner, N, et al., incorporated herein by reference. A borreliacidal factor in *Amblyomma americanum* saliva is associated with phospholipase $A_2$ activity, Zeidner, N, et al., *Experimental Parasitology*, 2009; 121(4):370-5, the entire contents of which are incorporated herein by reference as if each character were explicitly laid out herein. The results presented in FIG. 3 demonstrate that the borreliacidal factor found in *A. americanum* saliva is of protein origin.

Example 5

Comparative PAGE analysis of *A. americanum* and *I. scapularis* saliva demonstrate unique protein bands. Saliva of *A. americanum* and *I. scapularis* are analyzed by SDS-PAGE by methods known in the art and described by Zeidner, et al. 2009. Protein bands of approximately 120, 70, 31, 26, 23, and 21 kDa are identified in *A. americanum* saliva that are not recognized in saliva from *I. scapularis* (FIG. 4). A protein running at approximately 58-61 kDa is very prominent in *A. americanum* saliva when compared to *I. scapularis* (asterisks/arrow, FIG. 4).

Example 6

Gel filtration fractionation of *A. americanum* saliva produces individual fractions with borreliacidal activity. Saliva is fractionated into 11 molecular weight pools by gel filtration and then tested by a borreliacidal assay as described by Zeidner, et al. 2009. Briefly, *A. americanum* saliva is size fractionated on a Superdex 200 column run with 25 mM NaCl dissolved in 5 mM HEPES (pH 7.6) at a flow rate of 0.5 ml per minute. The separation is monitored at 280 nM. Fractions are collected at 1 minute intervals into siliconized eppendorf tubes. Each collected fraction is subsequently concentrated to 100 μl using a SpeedVac. 50 μl aliquots of the fractions are pooled according to the major molecular weight peaks at between 2 and 10 fractions per pool. Each pool is subsequently concentrated to 50 μl using Micron-3K filters (Millipore, Billerica, Mass.). Pools and then the individual component fractions of pools that demonstrate activity are then bioassayed for borreliacidal activity in vitro substantially as described in Example 4.

As noted in FIG. 5A, pools number 3 and 4 demonstrate significant borreliacidal activity compared to BSK-H controls. Only 69.4+/−7.3 percent of control spirochetes survive after 24 hrs of exposure to pool 3 ($p<0.025$), while exposure to pool 4 virtually eliminates all live spirochetes at 24 hrs post-incubation (2.7+/−0.8 percent of controls, $p<0.001$). Borreliacidal activity is not noted with any other pools when compared to media controls (FIG. 5A). Pool 3 demonstrates a higher molecular weight shoulder associated with pool 4 (data not shown), suggesting that the activity could result from a protein that overlaps both pools.

Fractions of pool 4 are further examined for borreliacidal assay (FIG. 5B). Two fractions demonstrate significant killing activity when compared to media controls at 24 hrs. Although quite diminished in activity when compared to the original pool 4, fractions numbered 2 (spirochete survival, 63.3+/−5 percent of control, $p<0.001$) and 5 (spirochete survival, 72.6+/−8 percent of control, $p<0.05$) demonstrate significant killing activity (FIG. 5B). Fractions numbered 1, 3 and 4 do not demonstrate any significant killing of spirochetes compared to media controls (FIG. 5B).

Example 7

Comparative 2D gel analysis of active and inactive saliva fractions derived from gel filtration identifies prominent peptides including phospholipase $A_2$. Individual fractions of pool 4 from Example 6 (numbered 1-5) are analyzed by 2-dimensional gel electrophoresis. As noted in FIG. 6A, a series of prominent peptides or protein are localized in the 38 kDa range (FIG. 6A, arrow) and in the 58-62 kDa molecular weight range (circle) when borreliacidal fractions numbered 2 and 5 are combined and analyzed by two-dimensional PAGE. When compared to a 2-dimensional PAGE which includes fractions 1, 3 and 4 (FIG. 6B), no protein or peptides are localized to these regions, suggesting the borreliacidal activity of *A. americanum* saliva represents proteins or peptides within this 38-62 kDa molecular weight range (FIG. 6A). The isoelectric point (pI) of these proteins is approximately 4.5-5.0.

Example 8

Figure 7:
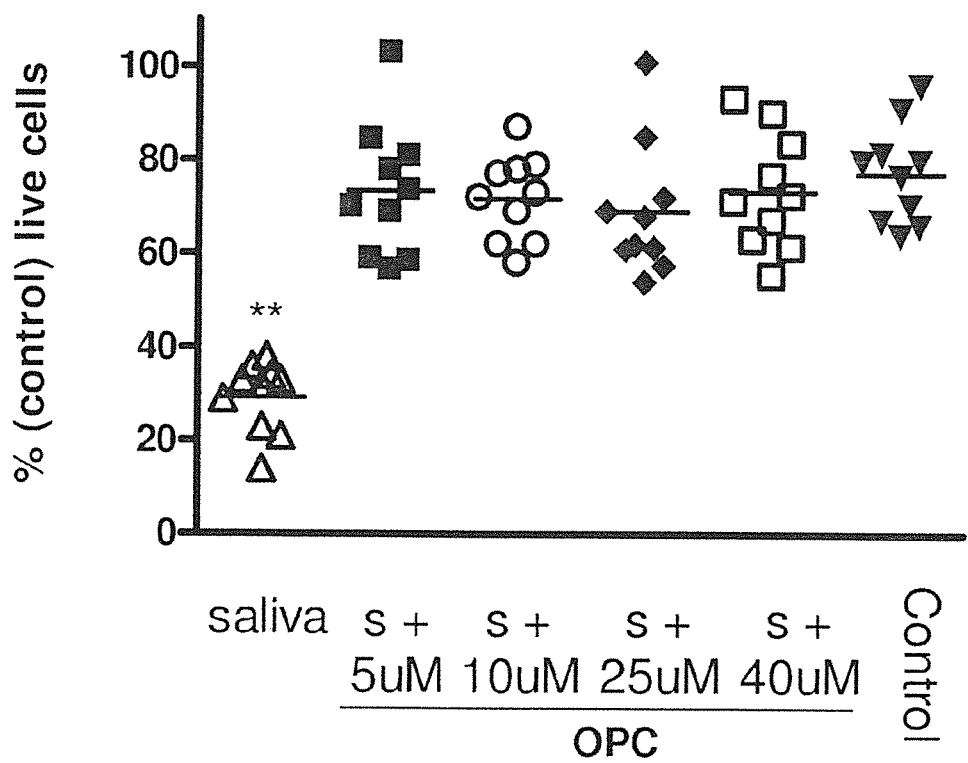
FIG. 7 represents inhibition of the borreliacidal activity of *A. americanum* saliva after incubation with oleyloxyethyl phosphorylcholine (OPC).

Inhibition of *A. americanum* borreliacidal activity using oleyloxyethyl phosphorylcholine (OPC) identifies phospholipase $A_2$ as an active component of *A. americanum* saliva. The borreliacidal assay of Example 6 is performed comparing saliva alone with saliva plus the phospholipase $A_2$ inhibitor OPC. At 24 hrs post incubation with saliva alone, the borreliacidal effect of *A. americanum* saliva (percent control live spirochetes, 30+/−7) is completely eliminated with concentrations of OPC ranging from 5-40 µM (percent control live spirochetes, 76-78, $p<0.0001$, FIG. 7). The percent control live spirochete numbers after incubation with saliva plus OPC are not significantly different than culture controls (79, $p=0.45$). As noted in FIG. 7, no titration effect is observed using concentrations of OPC ranging from 5-40 µM. These data demonstrate that the borreliacidal activity of *A. americanum* saliva is dependent on the enzymatic activity of phospholipase $A_2$.

The invention is hereby described with relation to the following references and those otherwise identified in the instant specification. Each reference is incorporated herein by reference as if each were laid out explicitly in its entirety in the instant specification including both text and figures. Each reference is incorporated for the individual point referred to in the specification as well as for all information contained therein and not explicitly identified in the specification. All references are representative of the knowledge of a person of skill in the art and illustrate other aspects of the present invention as envisioned by the inventors.

It is appreciated that all reagents are obtainable by sources known in the art unless otherwise specified. Methods of nucleotide amplification, cell transfection, and protein expression and purification are similarly within the level of skill in the art.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

REFERENCES

Anderson, J. F. & Magnarelli, L. A. (1980) Vertebrate host relationships and distribution of ixodid ticks (Acari: Ixodidae) in Connecticut, USA. *Journal of Medical Entomology*, 17, 314-23.

Anderson, B. E., Sims, K. G., Olson, J. G., Childs, J. E., Piesman, J. F., Happ, C. M., Maupin, G. O. & Johnson, B. J. (1993) *Amblyomma americanum*: a potential vector of human ehrlichiosis. *American Journal of Tropical Medicine and Hygiene*, 49, 239-44.

Armstrong, P. M., Brunet, L. R., Spielman, A. & Telford, S. R. (2001) 3rd Risk of Lyme disease: perceptions of residents of a Lone Star tick-infested community. *Bulletin of the World Health Organization*, 79, 916-25.

Arzt, E. S., Fernandez-Castelo, S., Diaz, A., Finkielman, S. & Nahmod, V. E. (1989) The muscarinic agonist pilocarpine inhibits DNA and interferon-gamma synthesis in peripheral blood mononuclear cells. *International Journal of Immunopharmacology*, 11, 275-81.

Barbour, A. G., Maupin, G. O., Teltow, G. J., Carter, C. J. & Piesman, J. (1996) Identification of an uncultivable *Borrelia* species in the hard tick *Amblyomma americanum*: possible agent of a Lyme disease-like illness. *Journal of Infectious Diseases*, 173, 403-9.

Bishopp, F. C. & Trembley, H. L. (1945) Distribution and hosts of certain North American ticks. *Journal of Parasitology*, 31, 1-54. Burgdorfer, W. (1975) A review of Rocky Mountain spotted fever (tick-borne typhus), its agent, and its tick vectors in the United States. *Journal of Medical Entomology*, 12, 269-78.

Burkot, T. R., Mullen, G. R., Anderson, R., Schneider, B. S., Happ, C. M. & Zeidner, N. S. (2001) *Borrelia lonestari* DNA in adult *Amblyomma americanum* ticks, Alabama. *Emerging Infectious Diseases*, 7, 471-3.

Calhoun, E. L. (1954) Natural occurrence of tularemia in the lone star tick, *Amblyomma americanum* (Linn.), and in dogs in Arkansas. *American Journal of Tropical Medicine and Hygiene*, 3, 360-6.

Childs, J. E. & Paddock, C. D. (2003) The ascendancy of *Amblyomma americanum* as a vector of pathogens affecting humans in the United States. *Annual Review of Entomology*, 48, 307-37.

Clark, K. L., Oliver, J. H. Jr, Grego, J. M., James, A. M., Durden, L. A. & Banks, C. W. (2001) Host associations of ticks parasitizing rodents at *Borrelia burgdorferi* enzootic sites in South Carolina. *Journal of Parasitology*, 87, 1379-86.

Clymer, B. C., Howell, D. E. & Hair, J. A. (1970) Environmental alteration in recreational areas by mechanical and chemical treatment as a means of lone star tick control. *Journal of Economic Entomology*, 63, 504-9.

Cooley, R. A. & Kohls, G. M. (1944) The genus *Amblyomma* (Ixodidae) in the United States. *Journal of Parasitology*, 30, 77-111.

Coons, L. B., Rosell-Davis, R. & Tarnowksi, B. I. (1986) Bloodmeal digestion in ticks. *Morphology, Physiology, and Behavioral Biology of Ticks* J. R. Sauer and J. A. Hair), pp. 248-279. John Wiley & Sons, New York.

Ewing, C., Scorpio, A., Nelson, D. R. & Mather, T. N. (1994) Isolation of *Borrelia burgdorferi* from saliva of the tick vector, *Ixodes scapularis*. *Journal of Clinical Microbiology*, 32, 755-8.

Feir, D., Santanello, C. R., Li, B. W., Xie, C. S., Masters, E., Marconi, R. & Weil, G. (1994) Evidence supporting the presence of *Borrelia burgdorferi* in Missouri. *American Journal of Tropical Medicine and Hygiene*, 51, 475-82.

Ginsberg, H. S., Ewing, C. P., O'Connell, A. F. Jr, Bosler, E. M., Daley, J. G. & Sayre, M. W. (1991) Increased population densities of *Amblyomma americanum* (Acari: Ixodidae) on Long Island, N.Y. *Journal of Parasitology*, 77, 493-5.

Hair, J. A. & Bowman, J. L. (1986) Behavioral ecology of *Amblyomma americanum* (L.). *Morphology, Physiology, and Behavioral Biology of Ticks* J. R. Sauer and J. A. Hair), pp. 406-427. John Wiley & Sons, New York.

Keirans, J. E. & Lacombe, E. H. (1998) First records of *Amblyomma americanum, Ixodes (Ixodes) dentatus*, and *Ixodes* (Cemtixodes) *uriae* (Acari: Ixodidae) from Maine. *Journal of Parasitology*, 84, 629-31.

Levine, J. F., Sonenshine, D. E., Nicholson, W. L. & Turner, R. T. (1991) *Borrelia burgdorferi* in ticks (Acari: Ixodidae) from coastal Virginia. *Journal of Medical Entomology*, 28, 668-74.

Luckhart, S., Mullen, G. R., Durden, L. A. & Wright, J. C. (1992) *Borrelia* sp. in ticks recovered from white-tailed deer in Alabama. *Journal of Wildlife Diseases*, 28, 449-52.

Luckhart, S., Mullen, G. R. & Wright, J. C. (1991) Etiologic agent of Lyme disease, *Borrelia burgdorferi*, detected in ticks (Acari: Ixodidae) collected at a focus in Alabama. *Journal of Medical Entomology*, 28, 652-7.

Madden, R. D., Sauer, J. R. & Dillwith, J. W. (2002) A proteomics approach to characterizing tick salivary secretions. *Experimental and Applied Acarology*, 28, 77-87.

Magnarelli, L. A., Anderson, J. F., Apperson, C. S., Fish, D., Johnson, R. C. & Chappell, W. A. (1986) Spirochetes in ticks and antibodies to *Borrelia burgdorferi* in white-tailed deer from Connecticut, New York State, and North Carolina. *Journal of Wildlife Diseases*, 22, 178-88.

Mather, T. N. & Mather, M. E. (1990) Intrinsic competence of three ixodid ticks (Acari) as vectors of the Lyme disease spirochete. *Journal of Medical Entomology*, 27, 646-50.

McMullen, H. L. & Sauer, J. R. (1978) The relationship of phosphodiesterase and cyclic AMP to the process of fluid secretion in the salivary glands of the ixodid tick *Amblyomma americanum*. *Experientia*, 34, 1030-31.

Mukolwe, S. W., Kocan, A. A., Barker, R. W., Kocan, K. M. & Murphy, G. L. (1992) Attempted transmission of *Borrelia burgdorferi* (Spirochaetales: Spirochaetaceae) (JDI strain) by *Ixodes scapularis* (Acari: Ixodidae), *Dermacentor variabilis*, and *Amblyomma americanum*. *Journal of Medical Entomology*, 29, 673-7.

Murphy, G. L., Ewing, S. A., Whitworth, L. C., Fox, J. C. & Kocan, A. A. (1998) A molecular and serologic survey of *Ehrlichia canis, E. chaffeensis*, and *E. ewingii* in dogs and ticks from Oklahoma. *Veterinary Parasitology*, 79, 325-39.

Oliver, J. H. Jr, Chandler, F. W. Jr, Luttrell, M. P., James, A. M., Stallknecht, D. E., McGuire, B. S., Hutcheson, H. J., Cummins, G. A. & Lane, R. S. (1993) Isolation and transmission of the Lyme disease spirochete from the southeastern United States. *Proceedings of the National Academy of Sciences of the USA*, 90, 7371-5.

Oliver, J. H. Jr, Magnarelli, L. A., Hutcheson, H. J. & Anderson, J. F. (1999) Ticks and antibodies to *Borrelia burgdorferi* from mammals at Cape Hatteras, N.C. and Assateague Island, Md. and Va. *Journal of Medical Entomology*, 36, 578-87.

Ouellette, J., Apperson, C. S., Howard, P., Evans, T. L. & Levine, J. F. (1997) Tick-raccoon associations and the potential for Lyme disease spirochete transmission in the coastal plain of North Carolina. *Journal of Wildlife Diseases*, 33, 28-39.

Piesman, J. (1993) Standard system for infecting ticks (Acari: Ixodidae) with the Lyme disease spirochete, *Borrelia burgdorferi*. *Journal of Medical Entomology*, 30, 199-03.

Piesman, J. & Happ, C. M. (1997) Ability of the Lyme disease spirochete *Borrelia burgdorferi* to infect rodents and three species of human-biting ticks (blacklegged tick, American dog tick, lone star tick) (Acari: Ixodidae). *Journal of Medical Entomology*, 34, 451-6.

Piesman, J., Maupin, G. O., Campos, E. G. & Happ, C. M. (1991) Duration of adult female *Ixodes dammini* attachment and transmission of *Borrelia burgdorferi*, with description of a needle aspiration isolation method. *Journal of Infectious Diseases*, 163, 895-7.

Piesman, J. & Sinsky, R. J. (1988) Ability of *Ixodes scapularis, Dermacentor variabilis*, and *Amblyomma americanum* (Acari: Ixodidae) to acquire, maintain, and transmit Lyme disease spirochetes (*Borrelia burgdorferi*). *Journal of Medical Entomology*, 25, 336-9.

Rawlings, J. A. & Teltow, G. J. (1994) Prevalence of *Borrelia* (Spirochaetaceae) spirochetes in Texas ticks. *Journal of Medical Entomology*, 31, 297-301.

Ribeiro, J. (1995) How ticks make a living. *Parasitology Today*, 11, 91-93.

Ribeiro, J. M., Makoul, G. T., Levine, J., Robinson, D. R. & Spielman, A. (1985) Antihemostatic, antiinflammatory, and immunosuppressive properties of the saliva of a tick, *Ixodes dammini*. *Journal of Experimental Medicine*, 161, 332-44.

Ribeiro, J., Mather, T. N., Piesman, J. & Spielman, A. (1987) Dissemination and salivary delivery of Lyme disease spirochetes in vector ticks (Acari: Ixodidae). *Journal of Medical Entomology*, 24, 201-5.

Ribeiro, J. M., Zeidner, N. S., Ledin, K., Dolan, M. C. & Mather, T. N. (2004) How much pilocarpine contaminates pilocarpine-induced tick saliva? *Medical and Veterinary Entomology*, 18, 20-4.

Ryder, J. W., Pinger, R. R. & Glancy, T. (1992) Inability of *Ixodes cookei* and *Amblyomma americanum* nymphs (Acari: Ixodidae) to transmit *Borrelia burgdorferi*. *Journal of Medical Entomology*, 29, 525-30.

Sanders, F. H. Jr & Oliver, J. H. Jr (1995) Evaluation of *Ixodes scapularis, Amblyomma americanum*, and *Dermacentor variabilis* (Acari: Ixodidae) from Georgia as vectors of a Florida strain of the Lyme disease spirochete, *Borrelia burgdorferi*. *Journal of Medical Entomology*, 32, 402-6.

Sauer, J. R. & Hair, J. A. (1972) The quantity of blood ingested by the lone star tick (Acarina: Ixodidae). *Annals of the Entomological Society of America*, 65, 1065-8.

Schulze, T. L. Lakat, M. F. W. E. Shisler, J. K., D. J. &, E. M. (1986) Comparison of rates of infection by the Lyme disease spirochete in selected populations of *Ixodes dammini* and *Amblyomma americanum* (Acari: Ixodidae). *Zentralblatt fur Bakteriologie, Mikrobiologie, and Hygiene Series A*, 263, 72-8.

Sonenshine, D. E. (1991) *Biology of Ticks*, Vol. 1. Oxford University Press, New York, pp. 119-188.

Sonenshine, D. E., Ratzlaff, R. E., Troyer, J., Demmerle, S., Demmerle, E. R., Austin, W. E., Tan, S., Annis, B. A. & Jenkins, S. (1995) *Borrelia burgdorferi* in eastern Virginia: comparison between a coastal and inland locality. *American Journal of Tropical Medicine and Hygiene*, 53, 123-33.

Stromdahl, E. Y., Evans, S. R., O'Brien, J. J. & Gutierrez, A. G. (2001) Prevalence of infection in ticks submitted to the human tick test kit program of the U.S. Army Center for Health Promotion and Preventive Medicine. *Journal of Medical Entomology*, 38, 67-74.

Teltow, G. J., Fournier, P. V. & Rawlings, J. A. (1991) Isolation of *Borrelia burgdorferi* from arthropods collected in Texas. *American Journal of Tropical Medicine and Hygiene*, 44, 469-74.

Valenzuela, J. G., Francischetti, I. M., Pham, V. M., Garfield, M. K., Mather, T. N. & Ribeiro, J. M. (2002) Exploring the sialome of the tick *Ixodes scapularis*. *Journal of Experimental Biology*, 205, 2843-64.

Varela, A. S., Luttrell, M. P., Howerth, E. W., Moore, V. A., Davidson, W. R., Stalknecht, D. E. & Little, S. E. (2004) First culture isolation of *Borrelia lonestari*, putative agent of southern tick-associated rash illness. *Journal of Clinical Microbiology*, 42, 1163-69.

Wikel, S. K. (1999) Tick modulation of host immunity: an important factor in pathogen transmission. *International Journal of Parasitology*, 29, 851-9.

Wolfinger, R. & O'Connell, M. (1993) Generalized linear mixed models: a pseudo-likelihood approach. *Journal of Statistical Computation and Simulation*, 48, 223-43.

Zeidner, N. S., Schneider, B. S., Nuncio, M. S., Gem, L. & Piesman, J. (2002) Coinoculation of *Borrelia* spp. with tick salivary gland lysate enhances spirochete load in mice and is tick species-specific. *Journal of Parasitology*, 88, 1276-8.

Zeidner N, Ullmann A, Sackal C, Dolan M, Dietrich G, Piesman J, Champagne D., (2009) A borreliacidal factor in *Amblyomma americanum* saliva is associated with phospholipase A2 activity. *Exp Parasitol.*, 121(4):370-5.

Zhu, K., Dillwith, J. W., Bowman, A. S. & Sauer, J. R. (1997) Identification of hemolytic activity in saliva of the lone star tick (Acari: Ixodidae). *Journal of Medical Entomology*, 34, 160-6.

The invention claimed is:

1. A process of altering the viability of a bacterial organism comprising:
   contacting a bacterial organism that is a member of the Spirochaetaceae family or the Treponemataceae family by administering to a vertabrate host infected with the bacterial organism a salivary protein derived from *Amblyomma americanum* (*A. americanum*) wherein said protein has phospholipase $A_2$ (PLA2)-like activity.

2. The process of claim 1 wherein said protein has a migratory molecular weight of between 53 and 69 kDA.

3. The process of claim 1 wherein said bacterial organism is *Borrelia burgdorferi, Borrelia crocidurae, Borrelia lusitaniae, Borrelia recurrentis, Borrelia hermsii, Borrelia parkeri, Borrelia lonestari, Borrelia afzelii, Borrelia garinii, Borrelia recurrentis, Borrelia buccalis, Borrelia refringens, Staphylococcus aureus* (*S. aureus*), *Escherichia coli* (*E. coli*), *Listeria monocytogenes* (*L. monocytogenes*), *Salmonella choleraesuis* (*S. choleraesuis*), *Salmonella typhi* (*S. typhi*), *Salmonella enteriditis* (*S. enteritidis*), *Salmonella pullorum* (*S. pullorum*), *Bacillus anthracis*, or *Mycobacterium tuberculosis* (*M. tuberculosis*).

4. The process of claim 3 wherein said bacterial organism is *Borrelia burgdorferi*.

5. The process of claim 1 wherein said salivary protein is at a concentration of from about 0.05 to about 10,000 micrograms/milliliter.

6. The process of claim 1 wherein said step of administering is one to three times per day.

7. The process of claim 1 wherein said salivary protein is at a concentration of 0.05 to 10,000 micrograms/milliliter.

8. The process of claim 1 wherein said contacting treats Lyme Disease in said vertebrate host.

9. A process for treating Lyme Disease in a vertebrate host comprising administering to the vertebrate host an effective amount of a composition comprising a suitable immunogenic carrier and an isolated phospholipase $A_2$-like protein derived from *Amblyomma americanum* (*A. americanum*).

10. The process of claim 9 wherein said administering comprises administering said composition to said vertebrate host between one to three times per day.

* * * * *